(12) United States Patent
Alviar et al.

(10) Patent No.: US 6,413,545 B1
(45) Date of Patent: Jul. 2, 2002

(54) DIET COMPOSITION AND METHOD OF WEIGHT MANAGEMENT

(75) Inventors: Barbara Alviar; Lynne Marie Connor, both of Rockford, MI (US); Albert Augustus Dixon, Tustin; Molly Marie Magee, Aliso Viejo, both of CA (US); Eugene Robert Maly, Kentwood; Suzanne M. McLauchlan, Ada, both of MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 09/786,099

(22) PCT Filed: Sep. 1, 1999

(86) PCT No.: PCT/US99/20116

§ 371 (c)(1),
(2), (4) Date: May 8, 2001

(87) PCT Pub. No.: WO00/12080

PCT Pub. Date: Mar. 9, 2000

Related U.S. Application Data

(60) Provisional application No. 60/098,715, filed on Sep. 1, 1998.

(51) Int. Cl.⁷ .............................................. A61K 47/00
(52) U.S. Cl. ................... 424/451; 424/400; 424/439; 424/484; 424/489; 424/514; 424/951
(58) Field of Search ................ 424/400, 439, 424/484, 489, 78.01; 514/951

(56) References Cited

U.S. PATENT DOCUMENTS

| | | |
|---|---|---|
| 3,764,692 A | 10/1973 | Lowenstein |
| 4,315,927 A | 2/1982 | Evans |
| 4,684,522 A | 8/1987 | Marissal et al. |
| 4,761,286 A | 8/1988 | Hiji |
| 5,017,614 A | 5/1991 | Pariza et al. |
| 5,087,623 A | 2/1992 | Boynton et al. |
| 5,087,624 A | 2/1992 | Boynton et al. |
| 5,124,357 A | 6/1992 | Newton et al. |
| RE33,988 E | 7/1992 | Evans |
| 5,164,384 A | 11/1992 | Paul |
| 5,165,935 A | 11/1992 | Andre et al. |
| 5,175,156 A | 12/1992 | Boynton et al. |
| 5,428,072 A | 6/1995 | Cook et al. |
| 5,430,066 A | 7/1995 | Cook et al. |
| 5,484,593 A | 1/1996 | Iwasaki et al. |
| 5,543,405 A | 8/1996 | Keown et al. |
| 5,550,113 A | 8/1996 | Mann |
| 5,554,646 A | 9/1996 | Cook et al. |
| 5,585,400 A | 12/1996 | Cook et al. |
| 5,612,039 A | 3/1997 | Policappelli et al. |
| 5,626,849 A | 5/1997 | Hastings et al. |
| 5,674,901 A | 10/1997 | Cook et al. |
| 5,688,784 A | 11/1997 | McNeill et al. |

OTHER PUBLICATIONS

Trent–LK; "Effects of Chromium Picolinate on Body Composition;" J–Sports–Med–Phys–Fitness., Dec. 1995; 35(4): 273–80 (Abstract).

Sabinsa Corporation; "Bis–Glycinato–Oxovanadium (BGOV) a New Nutraceutical from Sabinsa:" Jun. 1998.

Database HCAPLUS on STN, (Columbus, OH, USA), No. 129:321142, Mizusaki, S. 'Obesity preventive agents containing extracts of Garcinia cambogia and mulberry tree,' abstract, JP 10265397 A2, Sep. 6, 1998, see entire abstract.

Database HCAPLUS on STN, (Columbus, OH, USA), No. 128:192035, Wakamatsu, J. Antiobesity and diet food materials containing carinitine and bovine peptides, and foods containing them, abstract, JP 10066542 A2, Mar. 10, 1998, see entire abstract.

Database HCAPLUS on STN, (Columbus, OH, USA), No. 127:351178, Littera, R. 'Dietary composition containing chitosan, Garcinia cambogia hydroxycitrate, and organic chromium,' abstract, EP 803292 A2, Oct. 29, 1997, see entire abstract.

Database HCAPLUS on STN< (Columbus, OH, USA), No. 127:18U9791, Ueno, G. 'Effects of Gymnema sylvestre on obesity and diabetes,' abstract, kaguaku to Kogyo, 1997, see entire abstract.

Primary Examiner—Thurman K. Page
Assistant Examiner—Chareese Evans
(74) Attorney, Agent, or Firm—Amway Corporation

(57) ABSTRACT

A diet composition for managing body weight including effective amounts of *Garcinia cambogia* extract, *Gymnema sylvestre* extract, chromium picolinate, vanadium compound, L-carnitine, and conjugated linoleic acid. The daily effective amounts are administered in three approximately equal doses in conjunction with the daily meals. The diet composition is also administered in conjunction with a restricted-calorie diet. The diet composition optionally includes effective amounts of kola nut extract, dehydrated parsley, and lemon bioflavonoids.

16 Claims, No Drawings

DIET COMPOSITION AND METHOD OF WEIGHT MANAGEMENT

This application is a 371 of PCT/US99/20116, filed on Sep. 1, 1999, which claims benefit of 60/098,715, filed on Sep. 1, 1998.

BACKGROUND OF THE INVENTION

The present invention relates to a dietary supplement effective for managing body weight and to the method of managing body weight by administering the dietary supplement.

Many people attempt to control their body w eight in order to enhance personal health, appearance, and self image. Common methods to control or lose weight include one or more of the following: (1) a reduced-calorie diet that manages fat, carbohydrate, and protein intake, (2) pharmaceuticals, such as amphetamine-like agents to affect the hypothalamic center and reduce the hunger sensation, and (3) a physical activity/exercise program.

However, far too often individuals abandon a reduced-calorie diet regime before they reach their goal or ideal weight because they struggle against ingrained eating habits and feelings of hunger, emotional pressure, and discouragement. Further, the use of synthesized pharmaceuticals can stress the overall health and cause unwanted side effects, including addiction. Many individuals also fail to adhere to a physical activity regime over a long period.

Natural supplements can support weight management, for example, by affecting the body's metabolism or reducing appetite. A wide variety of formulations exist to supplement the diet to assist in the management of body weight. However, these formulations often focus on one or two components rather than a broad range of weight management supplements combined to provide an effective body weight management composition and method. For example, U.S. Pat. Nos. 5,428,072 and 5,554,646 to Cook disclose that conjugated linoleic acid ("CLA") reduces body fat and increases "feed efficiency." U.S. Pat. No. 3,764,692 to Lowenstein discloses that *Garcinia cambogia* contains hydroxy citric acid, which can be used to treat obesity by inhibiting fatty acid synthesis in the body. And U.S. Pat. No. 4,761,286 to Hiji discloses that *Gymnema sylvestre* extract inhibits the absorption of glucose through the intestinal tract and thus assists in prevention of obesity. However, Cook, Lowenstein, and Hiji fail to suggest combinations with other weight management supplements that together are effective and safe to reduce or control weight.

The existing natural-supplement formulations that combine several supplements fail to provide the advantages of enhanced and efficient body weight management through a range of effective and supportive supplements. For example: 1) U.S. Pat. No. 5.612,039 to Policappelli discloses a weight control supplement that combines *Garcinia cambogia* extract with numerous herbal components. 2) U.S. Pat. No. 5,626,849 to Hasting discloses a dietary supplement combining hydroxy citric acid, L-carnitine, choline, inositol, gamma-linolenic acid, *Ginkgo biloba* leaves, coenznme $Q_{10}$, and other components; 3) U.S. Pat. Nos. 5,614,224 and 5,730,988 to Womack disclose products combining L-carnitine, chromium picolinate, and vanadyl sulfate to aid diabetics by enhancing the positive effects of insulin; 4) U.S. Pat. No. 5,164,384 to Paul discloses a supplement combining chromium picolinate, vanadyl sulfate, and niacin to mimic insulin's positive effects on the body's metabolism; 5) Amway Corporation has sold in the U.S. for more than one year a dietary supplement in capsule form containing *Garcinia cambogia* extract, cayenne extract, alfalfa concentrate, and chromium picolinate; and 6) U.S. Pat. No. 5,543.405 to Keown discloses a weight reduction composition including ephedrine or caffeine combined with chromium picolinate or vanadyl salts administered in conjunction with a restricted-calorie diet. Therefore, a need still exists for an effective dietary supplement system providing a range of beneficial components to supplement an effective weight management program.

SUMMARY OF THE INVENTION

The aforementioned problems are overcome in the present invention wherein a body weight management composition includes effective amounts of *Garcinia cambogia* extract, *Gymnema sylvestre* extract, chromium picolinate, vanadium compound, L-carnitine, and conjugated linoleic acid ("CLA"). The body weight management composition may also include effective amounts of kola nut extract, dehydrated parsley, and lemon bioflavonoids.

The invention is also directed to a method of enhancing body weight management by orally administering the compositions described above. The effective daily amounts can be administered in three approximately equal doses taken from about two hours before to about 30 minutes after each daily meal. Preferably, the individual taking the body weight management composition also consumes a reduced-calorie daily diet in conjunction with the daily administration of the effective amounts.

The diet composition and method of body weight management of the present invention provide several advantages. The diet composition of the present invention enhances the dieting individual's ability to decrease body fat mass, decrease the level of triglycerides in the blood, decrease low-density lipoproteins (LDL) in the blood, increase body lean mass, and increase high-density lipoproteins (HDL) in the blood. Further, the diet composition supports and enhances the natural functions of the body to assist the individual to maintain and manage his or her desired body weight. The diet composition assists in reducing body fat by causing the human metabolism to more efficiently convert fat to lean muscle. The diet composition can be made to include only natural components in a conveniently administered capsule form.

Daily administration of the effective amounts of the composition to an individual on a restricted-calorie diet supports and enhances the dieting individual's ability to lose weight and maintain the weight loss. The diet composition can diminish the sense of hunger without including the pharmaceutical equivalent of amphetamines.

These and other objects, advantages, and features of the invention will be more readily understood and appreciated by reference to the detailed description of the preferred embodiments.

DETAILED DESCRIPTION OF THE PREFERRED EMBODIMENTS

The diet composition of the present invention contains several components provided in a mixture or separately for human oral consumption. The components include *Garcinia cambogia* extract, *Gymnema sylvestre* extract, chromium picolinate, vanadium compound, L-carnitine, conjugated linoleic acid (CLA), and other components discussed below. The effective daily amounts of the diet composition are preferably administered in three approximately equal doses over the period of a day in conjunction with a reduced calorie diet.

Garcinia Cambogia Extract

The diet composition of the present invention contains an amount of *Garcinia cambogia* extract effective in the supplement to support body weight management. "Body weight management" as used herein includes body weight loss, body weight control, body weight maintenance, body fat mass decrease, lean body mass increase, blood triglyceride level decrease, blood HDL level increase, blood LDL level decrease, reduction of fats in the bodily organs, blood pressure reduction, and the like.

*Garcinia cambogia*—also known as Malabar Tamarind or Brindall Berry—is a yellowish fruit that is about the size of an orange, with a thin skin and deep furrows similar to an acorn squash. Native to south India, *Garcinia cambogia* is dried and used extensively in curries and has been historically used in the Ayurvedic treatment of obesity.

*Garcinia cambogia* extract is a source of gamma-hydroxy citric acid, which is beneficial for weight loss due to appetite suppressant effects and inhibition of the synthesis of fatty acids in the liver. Gamma-hydroxycitrate may thus reduce serum lipids and body fat by reduced conversion of carbohydrates into fat. Although hydroxy citric acid is the principle acid that has been identified in *Garcinia cambogia* fruits, *Garcinia cambogia* contains other phytochemicals such as the lactone of gamma-hydroxy citric acid, cambogia and cambogia, garcinol and its isomer isogarcinol, and anthocyanin pigments.

The daily effective amount of *Garcinia cambogia* extract in the present supplement includes from about 392 to about 3,524 mg, preferably from about 1,175 to about 2,741 mg, more preferably from about 1,566 to about 2,350 mg, and most preferably about 1,958 mg. As used herein, "daily effective amounts" correlate to the average adult male human's weight and therefore, are adjustable to correlate with varying weights, as is known in the art.

*Garcinia cambogia* extracts and gamma-hydroxy citric acid are further described in U.S. Pat. No. 3,764,692 to Lowenstein entitled "Method of Treating Obesity" issued Oct. 9, 1973; U.S. Pat. No. 5,612,039 to Policappeli entitled "Dietary Supplement" issued Mar. 18, 1997; and U.S. Pat. No. 5,626,849 to Hastings entitled "Weight Loss Composition For Burning and Reducing Synthesis of Fats" issued May 6, 1997, each of which is incorporated herein by reference. *Garcinia cambogia* extract in granular form is available from Sabinsa Corporation of Piscataway, N.J.

Gymnema Sylvestre Extract

The diet composition also contains an amount of *Gymnema sylvestre* extract effective in the supplement to support body weight management. *Gymnema sylvestre* is a large, woody, much branched climber that grows in central and western India, tropical Africa, and Australia. The fresh plant material of *Gymnema sylvestre* has been found to contain gymnemic acids ($A_1$, III, IV, V, VIII, and IX), gymnemagenin, and gymnemasides.

The daily effective amount of *Gymnema sylvestre* extract in the present supplement includes from about 27 to about 293 mg, preferably from about 80 to about 186 mg, more preferably from about 106 to about 160 mg, and most preferably about 133 mg. *Gymnema sylvestre* extracts are further described in U.S. Pat. No. 4,761,286 to Hiji entitled "Intestinal Absorption Inhibiting Agent" issued Aug. 2. 1988; U.S. Pat. No. 5,484,593 to Iwasaki entitled "Diet Composition Comprising Gymnema Inodrum and Method of Suppressing the Absorption of Saccharides" issued Jan. 16, 1996; and U.S. Pat. No. 5,730,988 to Womack entitled "Nutritional Supplements for Improving Glucose Metabolism" issued Mar. 24, 1998, each of which is incorporated herein by reference. *Gymnema sylvestre* extract containing 75% gymnemic acids is available from Sabinsa Corporation.

Chromium Picolinate

The diet composition also includes an amount of chromium picolinate effective in the supplement to support body weight management. Chromium picolinate is a biologically active form of chromium, which many aid brain synthesis of serotonin, a neurotransmitter that helps control appetite and especially sugar cravings. Chromium picolinate may also help maintain a high metabolic rate to assist weight loss, increase lean body mass, and relieve undesirably high levels of lipids formed as a result of high levels of glucose. Optimal chromium nutrition may help promote efficient function of insulin's effect on the brain's weight-regulatory mechanism.

The daily effective amount of chromium picolinate in the present supplement includes from about 0.5 to about 4.5 mg, preferably from about 1.5 to about 3.5 mg, more preferably from about 2 to about 3 mg, and most preferably about 2.5 mg.

The use and derivation of chromium picolinate are further described in U.S. Pat. Nos. 5,087,623 and 5,087,624 to Boynton entitled "Chromic Picolinate Treatment" issued Feb. 11, 1992; U.S. Pat. No. 5,175,156 to Boynton entitled "Chromic Picolinate Treatment" issued Dec. 29, 1992; U.S. Pat. No. 5,164,384 to Paul entitled "Anabolic Mineral Formula" issued Nov. 17, 1992, and U.S. Pat. No. Re.33,988 to Evans entitled "Dietary Supplementation With Essential Metal Picolinates" issued Jul. 7, 1992, each of which is incorporated herein by reference. Chromium picolinate is available from Nutrition 21 Corporation.

Vanadium Compound

The diet composition also includes an amount of vanadium compound absorbable from the gastrointestinal tract to the bloodstream as a vanadium source effective in the supplement to support body weight management. Effective vanadium compounds include those set forth in U.S. Pat. No. 5,550,113 to Mann entitled "Blood Sugar Regulating Composition and Methods Relating Thereto" issued Aug. 27, 1996 and U.S. Pat. No. 5,688,784 to McNeill entitled "Method of Suppressing Appetite with Vanadium Complexes" issued Nov. 18, 1997, each of which is incorporated herein in its entirety by this reference. These effective vandium compounds include vanadium carbonyl, vanadium pentoxide, vanadium trisulfate, vanadyl dichloride, vanadyl trichloride, vanadyl glycinate, vanadyl luconate, vanadyl citrate, and vanadyl sulfate. Preferably, the vanadium compound is a water-soluble chelate of vanadium with amino acids. More preferably, the vanadium compound is bis-glycinato oxo vanadium ("BGOV"). BGOV is a form of organically-bound vanadium—namely, a vanadium complex with the amino acid glycine, containing 23% elemental vanadium. BGOV is available from Sabinsa Corporation of Piscataway, N.J.

The daily effective amount of vanadium compound includes from about 0.02 to about 0.16 mg, preferably from about 0.05 to about 0.13 mg, more preferably from about 0.07 to about 0.11 mg, and most preferably about 0.09 mg.

L-Carnitine Fumarate

The diet composition also includes an amount of L-carnitine effective in the supplement to support body weight management. L-carnitine is essential for the transfer of fat into the mitochondria for metabolism and energy release via beta-oxidation. It is also believed that L-carnitine may improve and maintain heart and vessel health.

The preferred L-carnitine is L-carnitine fumarate, a non-essential amino acid salt produced in the body from lysine and methionine. It is believed that L-carnitine fumarate supplementation may improve the aerobic function and blood lipid profile and have a beneficial effect on exercise performance. The use of L-carnitine fumarate is described in U.S. Pat. No. 5,614,224 to Womack entitled "Nutritional Supplement for Diabetics" issued Mar. 25, 1997 and U.S. Pat. No. 5,626,849 to Hastings entitled "eight Loss Composition for Burning and Reducing Synthesis of Fats" issued May 6, 1997, both of which are incorporated herein by reference. L-carnitine fumarate is available from Biosint Corporation.

The daily effective amount of L-carnitine fumarate includes from about 118 to about 1,060 mg, preferably from about 353 to 825 mg, more preferably from about 471 to about 707 mg, and most preferably about 589.

Conjugated Linoleic Acid

The diet composition includes an amount of conjugated linoleic acid ("CLA") effective in the supplement to support body weight management. CLA is believed to inhibit the body's mechanism for storing fat to cause the body to utilize fatty reserves for energy. CLA also increases lipase activity, an enzyme which breaks down fats stored in fat cells of the body. The fatty acids are returned to the bloodstream to be used as an energy source for muscle cells. In addition to reducing body fat, CLA is known to improve muscle tone, improve nutrient usage, and perform as a powerful antioxidant.

Since CLA is not produced in vivo in humans, it has to be obtained through the diet, for example, from consumption of beef and dairy fats. Typically, consumers do not consume enough CLA in a typical diet. CLA can be derived from the linoleic acid of vegetable oil—such as sunflower oil, corn oil, or safflower oil. CLA is available from PharmaNutrients under the TONALIN trademark. The use and derivation of CLA are described in U.S. Pat. No. 5,017,614 to Pariza entitled "Methods of Preventing Oxidation, Quenching Singlet Oxidation and Inhibiting Mold Growth and Novel Compositions Therefore" issued May 21, 1991; U.S. Pat. No. 5,070,104 to Pariza entitled "Methods of Chelating Metal and Novel Compositions Therefore" issued Dec. 3, 1991; U.S. Pat. No. 5,428,072 to Cook entitled "Method of Increasing the Efficiency of Feed Conversion in Animals" issued Jun. 27, 1995; U.S. Pat. No. 5,430,066 to Cook entitled "Methods for Preventing Weight Loss, Reduction in Weight Gain, and Anorexia Due to Immune Stimulation" issued Jul. 4, 1995; U.S. Pat. No. 5,554,646 to Cook entitled "Method for Reducing Body Fat in Animals" issued Sep. 10, 1996; U.S. Pat. No. 5,585,400 to Cook entitled "Methods of Attenuating the Allergic Response in Animals" issued Dec. 17, 1996; and U.S. Pat. No. 5,674,901 to Cook entitled "Methods of Treating Animals to Maintain or Increase CD-4 and CD-8 Cell Populations" issued Oct. 7, 1997, each of which is incorporated herein by reference.

The daily effective amount of CLA includes from about 360 to about 4,000 mg, preferably from about 1,080 to about 2,520 mg, more preferably from about 1,440 to about 2,160 mg, and most preferably about 1,800 mg.

Other Components

The diet composition may include amounts of kola nut extract, parsley, and lemon bioflavonoids effective in the supplement to support body weight management. The parsley is preferably heat-treated dehydrated parsley. The parsley dehydrate and lemon bioflavonoids contains antioxidants and other phytochemicals. Both are manufactured by the Nutrilite Division of Amway Corporation. The kola nut extract is a source of caffeine having stimulatory and anti-diuretic effects, and is available from Botanicals International having a 10% minimum caffeine content.

The daily effective amount of dehydrated parsley includes from about 41 to about 367 mg, preferably from about 122 to about 285 mg, more preferably from about 163 to about 245 mg, and most preferably about 204 mg. The daily effective amount of lemon bioflavonoids includes from about 12 to about 108 mg, preferably from about 36 to about 84 mg, more preferably from about 48 to about 78 mg, and most preferably about 60 mg. The daily effective amounts of kola nut extract include from about 66 to about 594 mg, preferably from about 198 to 462 mg, more preferably from about 264 to about 396 mg, and most preferably about 330 mg.

Manufacture

The diet composition can be produced in the form of gelatin capsules, hard capsules, pills, resins, or any other compressed material. The diet composition can be produced as a powder, liquid, syrup, emulsion, suspension, and any other available substance to produce finished food product. The diet composition can also be provided as part of food products, for example, in the form of biscuits, cakes, cookies, weight loss candy bars, or ingredients of beverages, pasta, or other solid, liquid, or powder carrier for the composition.

When manufactured as a powder supplied in natural gelatin capsules (e.g., clear two-piece hard-shell capsules) such as those available from Capsugel Corporation, the composition may include various pharmaceutically-acceptable excipients, fillers (e.g., microcrystalline cellulose), lubricants (e.g., magnesium stearate), and glydant/flow agents (e.g., silicone dioxide), as is known in the art.

The components of the dietary supplement can be supplied as a mixture or in various combinations in separate discreet forms such as capsules. The amount of supplement or components in any one capsule or tablet depends upon the size restriction of the tablet or capsule according to that acceptable to the consumer for oral consumption.

Method of Administering

The effective daily amounts of the diet composition can be administered in three approximately equal doses over the period of a day. Preferably, the doses are taken in the period of from about two hours before each daily meal to about 30 minutes after each daily meal, and more preferably administered about 30 minutes before each daily meal (i.e., breakfast, lunch, and dinner).

Preferably the effective daily amounts are administered to an individual consuming a reduced-calorie daily diet. For example, the reduced-calorie daily diet includes a daily calorie intake less than the daily caloric expenditure of the individual.

An optimal reduced-calorie diet includes healthy amounts of carbohydrates, proteins, and fats, as recommended by health authorities. An optim described, for example, in Better Life Institute, "Your Map to Health: A Guide to Fitness, Nutrition, and Wellness" (1998).

The reduced-calorie diet preferably includes at least 55% carbohydrates, with a variety of complex and simple carbohydrates, from about 15% to about 28% protein, and less than about 30% fat. The fat content, although low, contributes to the palatability of the diet, so that the dieter is more likely to maintain the reduced-calorie diet. The diet preferably also includes a nutritionally adequate number and amount of essential vitamins and minerals.

For example, a 1024-calorie daily diet may include 63.14 grams protein, 163.7 grams carbohydrate, and 16.32 grams fat (containing 4.93 grams saturated fat, 4.68 grams mono-unsaturated fat, 4.09 grams polyunsaturated fat and 2.62 grams other fat), and includes 89.20 mg cholesterol, 15.88 grams dietary fiber, and 88.04 grams sugar. Such a diet contains about 24% protein, 62% carbohydrates, and about 14% fat.

As another example, a 1001-calorie daily diet may include 73.83 grams protein, 164.20 grams carbohydrate, 11.40 grams fat (containing 2.74 grams saturated fat, 2.66 grams mono-unsaturated fat, 2.33 grams polyunsaturated fat, and 3.67 grams other fat), and includes 49.96 mg cholesterol, 20.74 grams dietary fiber, and 108.40 grams sugar. Such a diet contains about 28%, protein, about 62% carbohydrate, and about 10% fat.

A 1318-calorie daily diet may include 81.66 grams protein, 209.5 grams carbohydrate, and 21.02 grams fat (containing 6.58 gram, 6.21 grams mono-unsaturated fat, 4.67 grams polyunsaturated fat, and 3.56 grams other fat), and includes 105.5 mg cholesterol, 20.41 grams dietary fiber, and 110.10 grams sugar. Such a diet contains about 24% protein, about 62% carbohydrates, and about 14% fat.

A 1298-calorie daily diet may include 92.09 grams protein, 212.0 grams carbohydrate, and 15.38 grams fat (containing 3.96 grams saturated fat, 4.01 mono-unsaturated fat, 2.66 grams polyunsaturated fat and 4.75 grams other fat), and includes 62.24 mg cholesterol, 25.92 dietary fiber, and 130.80 grams sugar. Such a diet contains about 27% protein, about 63% carbohydrates, and about 10% fat.

A 1540-calorie daily diet may include 86.02 grams protein, 239.60 grams carbohydrate, and 32.31 grams fat (containing 7.27 grams saturated fat, 10.02 grams mono-unsaturated fat, 10.45 poly-unsaturated fat, and 4.57 grams other fat), and includes 155.8 mg cholesterol, 28.38 grams dietary fiber, and 122.0 grams sugar. Such a diet contains about 22% protein, about 60% carbohydrates, and about 18% fat.

A 1560-calorie daily diet may include 89.61 grams protein, 250.20 grams carbohydrate, 27.92 grams fat (containing 6.74 saturated fat, 8.42 grams mono-unsaturated fat, 8.17 grams poly-unsaturated fat, and 4.59 grams other fat), and includes 149 mg cholesterol, 33.07 grams dietary fiber, and 136 grams sugar. Such a diet contains about 22% protein, about 62% carbohydrates, and about 16% fat.

The dieter preferably supplements the diet with a multiple vitamin tablet that provides at least 22 essential vitamins and minerals, such as DOUBLE X multiple vitamin available from Amway Corporation.

A reduced calorie diet may include a granulated fiber product for sprinkling on foods (e.g., salads, yogurt) to improve fiber intake. Preferably the granulated fiber product also supports the growth of "friendly" bacteria in the intestine by inclusion of fructooligosaccharides (FOS), which enhance colon health. The granulated fiber product provides a concentrated source of fiber so that at least about 25% and preferably at least about 33% of the total weight of the granulated fiber product is fiber. Preferably, about 30 to 40% of the total dietary fiber in the granulated fiber product is soluble fiber (the balance being insoluble fiber).

The following table sets forth typical components and amounts for the fiber granulation product:

TABLE A

| Component | Range of component (weight percent) | Preferred (weight percent) |
|---|---|---|
| Rice Fiber Concentrate[1] | 30 to 45 | 37 |
| Oat Flour[2] | 7 to 14 | 10 |
| Oat Bran[3] | 3 to 7 | 6 |
| Chicory Root Extract (a fructooligo-saccharides source)[4] | 8 to 12 | 10 |
| Fiber Granulation (a mixture of other fiber sources such as Lemon fiber powder, corn bran, acerola cherry pulp powder, barley bran, carrot pulp powder) | 2 to 5 | 3 |
| Apple Fiber Flakes (dried) | 10 to 15 | 13 |
| Other Components such as molasses, honey, and processing aids | 3 to 35 | 23.00 |

[1]Available from FoodEx, Inc.
[2]Available from Quaker Oats Corporation.
[3]Available from Quaker Oats Corporation.
[4]Available from Rhone Poulenc under the trademark RAFTILINE.

The preferred amounts above provide about 32.2 grams total dietary fiber (TDF) per 100 grams serving. Amway Corporation provides a granulated fiber product that has the preferred attributes and components as set forth above under the trade name TRIM ADVANTAGE™ FIBER BITS™ Dietary Supplement.

A reduced-calorie diet may also include a nutritionally-balanced no-fat or low-fat drink that provides dietary fiber. One such type of drink is a fruit-based, ready to drink beverage that includes the following components:

TABLE B

| | Fruity Fiber Drink | | |
|---|---|---|---|
| Component | Range weight percent | Preferred weight percent | Comment |
| Benefiber RV (partially hydrolyzed guar gum) | 1 to 4 | 1.5 | In a 250 ml serving, this provides 5 grams of fiber or about 20% of the recommended daily value. |
| Gum Arabic | 0.5 to 3 | 1.00 | |
| Sweetener (selected from one or more of the following: High Fructose Corn Syrup, Sucrose, | 0.10 to 15 | 0.10 (sucralose) 13 (fructose) | The sweetener is present in an amount suitable to taste. If the sweetener is sucralose, a suitable amount is about 0.10 to 0.50. If the sweetener is fructose, a suitable |

TABLE B-continued

Fruity Fiber Drink

| Component | Range weight percent | Preferred weight percent | Comment |
|---|---|---|---|
| Sucralose, or other natural or artificial sweeteners) | | | amount is about 10 to 15% |
| Fruit juices | 1 to 7 | 2 | One suitable combination of fruit juices is about 1.69% aronia berry and 0.23% white grape juice. Another suitable combination is about 2.64% cranberry juice and 2.55% apple juice. |
| Citric acid | 0.05 to 0.50 | .2 | |
| Calcium and magnesium salts | 0.75 to 2.00 | 1.2 | A suitable combination is about 0.89% of Calcium Lactate and 0.27% of Magnesium Lactate. |
| Water | Balance | Balance | |

A reduced-calorie diet may also include nutritionally-balanced meal replacement drinks. Typically, a meal replacement drink is provided either ready to drink or in powder form that is mixed with milk or water. These drinks usually provide a large percentage of the recommended daily values for fiber, protein (amino acids), vitamins and minerals. Amway Corporation provides a variety of low-fat drink mixes having the attributes set forth above under the TRIM ADVANTAGE™ and POSITRIM® brands.

The following example is presented for the purpose of further illustrating and explaining the present invention and is not to be taken as limiting in any regard. Unless otherwise indicated, all parts and percentages are by weight.

EXAMPLE

The following diet composition capsules were administered to 28 moderately or markedly obese (but otherwise healthy) individuals in conjunction with a reduced-calorie diet over six weeks. The participants were both male and female; 25% were 18 to 30 years in age, 50% were 31 to 55 years in age, and 25% were over 56 years in age. Each individual consumed one Capsule A, one Capsule B, and two Capsules C taken together three times a day and approximately one-half hour before meals. The capsules were taken with about 8 fluid ounces of water.

Capsule A contained the approximate amount of ingredients as shown in Table C.

TABLE C

| | Capsule A | | |
|---|---|---|---|
| Component | Weight Percent | Weight (mg) | Comment |
| Garcinia Cambogia Extract | 54.06 | 306 | Source of (−) hydroxy citric acid; Sabinsa Corporation |
| Gymnema Sylvestre Extract | 7.85 | 44.44 | Contains 75% gymnemic acids; Sabinsa Corporation |
| Parsley Dehydrate (heat-treated) | 6.01 | 34.00 | Phytochemicals, Amway Corporation |
| Chromium Picolinate | 0.15 | 0.84 | Source of chromium; Nutrition 21 Corporation |
| Bis-Glycinato Oxo Vanadium (BGOV) | 0.01 | 0.03 | Source of vanadium; Sabinsa Corporation |
| Microcrystalline Cellulose, Granular | 9.36 | 53.00 | Degussa (Elcema G-250) |
| Microcrystalline Cellulose, Powder | 4.27 | 24.18 | Degussa (Elcema P-100) |
| Magnesium Stearate, Vegetable | 0.88 | 5.00 | Mallinockodt |
| Silicon Dioxide, Fine Powder | 0.44 | 2.50 | Grace Davison (Syloid 244 FP) |
| Two-piece hard shell gelatin capsule | 16.96 | 96.00 | Capsugel Corporation |
| Total | 100% | 566 mg | |

The Capsule B contained the approximate amount of ingredients as shown in Table D.

TABLE D

| Component | Capsule B | | Comment |
|---|---|---|---|
| | Weight Percent | Weight (mg) | |
| Garcinia Cambogia Extract | 40.45 | 346.67 | Source of gamma-hydroxy citric acid; Sabinsa Corporation |
| L-Carnitine Fumarate | 22.94 | 196.58 | Biosint Corporation |
| Kola Nut Dry Extract, Powder | 12.84 | 110 | >10% caffeine; Botanicals International |
| Parsley Powder (dehydrate, heat-treated) | 3.97 | 34.0 | Phytochemicals; Amway Corporation |
| Microcrystalline Cellulose, Powder | 2.50 | 21.40 | Degussa (Elcema P-100) |
| Microcrystalline Cellulose, Granular | 2.44 | 20.91 | Degussa (Elcema G-250) |
| Magnesium Stearate, Vegetable | 0.88 | 7.50 | Mallinderodt |
| Silicon Dioxide, NF Fine Powder | 0.34 | 2.94 | Grace Davison (Syloid 244FP) |
| Natural Gelatin Two-Piece Hard-shell Capsule | 13.65 | 117 | Capsugel Corporation |
| Total | 100% | 857 mg | |

Capsule C contained the approximate amount of ingredients as shown in Table E.

TABLE E

| Component | Capsule C | | Comment |
|---|---|---|---|
| | Weight Percent | Weight (mg) | |
| Sunflower Oil containing 60% Conjugated Linoleic Acid (CLA) | 82.3 | 525 | 60% CLA; PharmaNutrients Corporation |
| Lemon Bioflavonoids | 3.1 | 20 | Amway Corporation |
| Bees Wax | 12.2 | 78 | |
| Lecithin | 2.4 | 15 | |

The 28 participants consumed meals together with capsules taken daily as described above: (1) for two weeks in conjunction with an about 1000-calorie diet having about 28% protein, about 62% carbohydrate, and about 10% fat; (2) for the following two weeks in conjunction with an about 1300-calorie diet having about 27% protein, about 63% carbohydrate, and about 10% fat; and (3) for the next two weeks in conjunction with 1560-calorie diet having about 22% protein, about 62% carbohydrate, and about 16% fat.

The weight management system was effective in reducing weight and body mass during the six-week study. The treatment was well tolerated. After the first two weeks, 46% of the participants reported that the supplements decreased their appetite (compared to 19% reporting an appetite increase and 35% no effect on appetite). After the second two weeks, 54% of the participants reported that the supplements decreased their appetite (compared to 8% reporting an appetite increase and 38% no effect on appetite). After the third two-week period, 46% reported that the supplements decreased their appetite (compared to 4% reporting an appetite increase and 50% no effect on appetite). Table F shows additional results of the study.

TABLE F

Study Results

| Variable | Decrease from Baseline | | |
|---|---|---|---|
| | 2 Weeks | 4 Weeks | 6 Weeks |
| Body Mass Index | 1.1 | 1.43 | 1.71 |
| % Body Fat | <0.01> | 0.20 | 0.67 |
| Weight (kg) | 3.13 | 4.12 | 4.94 |
| Fat Mass (kg) | 1.22 | 1.85 | 2.61 |
| Lean Body Mass (kg) | 1.90 | 2.27 | 2.34 |
| % Weight Decrease | 3.45 | 4.47 | 5.37 |
| Cholesterol (mg/dL) | 38.9 | 40.4 | 39.8 |
| HDL Cholesterol (mg/dL) | 3.1 | 6.5 | 5.2 |
| LDL Cholesterol (mg/dL) | 24.5 | 26.4 | 27.2 |
| Triglycerides (mg/dL) | 56.9 | 37.8 | 39.1 |
| Systolic Blood Pressure | 4.5 | 5.7 | 2.9 |
| Diastolic Blood Pressure | 2.3 | 3.1 | 4.0 |

Although the invention has been described with respect to dietary control for humans, the composition has application for other animals, for example to enhance the body weight management of canine, bovine, feline, and equine animals. When used for animals, the quantity of the composition will vary according to the different metabolisms and body weights of the animals.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents.

The embodiments of the invention in which an exclusive property or privilege is claimed are defined as follows:

1. A method of body weight management for an individual comprising: orally administering to the individual daily amounts of from about 1,175 to about 2,741 mg *Garcinia cambogia* extract, from about 80 to about 186 mg *Gymnema sylvestre* extract, from about 1.5 to about 3.5 mg chromium picolinate, from about 0.05 to about 0.13 mg bis-glycinato oxo vanadium, from about 353 to about 825 mg L-carnitine fumarate, from about 1,080 to about 2,520 mg conjugated linoleic acid, from about 264 to about 396 mg kola nut extract, from about 163 to about 245 mg dehydrated parsley, and from about 48 to about 72 mg lemon bioflavonoids; and simultaneously restricting the individual to a reduced-calorie diet in which the daily caloric intake is less than the daily caloric expenditure of the individual.

2. The method of claim 1 wherein said daily amounts are administered in at least three approximately equal doses within the time period of from about two hours before each daily meal to about 30 minutes after each daily meal.

3. The method of claim 1 wherein said daily amounts are administered about 30 minutes before each daily meal.

4. The method of claim 1 wherein the daily amounts comprise from about 1,566 to about 2,350 mg Garcinia cambogia extract, from about 106 to about 160 mg Gymnema sylvestre extract, from about 2 to about 3 mg chromium picolinate, about 0.07 to about 0.11 mg vanadium compound, from about 471 to about 707 mg L-carnitine, and from about 1,440 to about 2,160 mg conjugated linoleic acid.

5. The method of claim 4 wherein said daily amounts include about 1,958 mg Garcinia cambogia extract, about 133 mg Gymnema sylvestre extract, about 2.5 mg chromium picolinate, about 0.09 mg water-soluble chelate of vanadium and amino acid, about 589 mg L-canitine fumarate, and about 1,800 mg conjugated linoleic acid.

6. The method of claim 4 wherein said reduced-calorie diet is no more than about 1,550 calories per day.

7. The method of claim 6 wherein said reduced calorie diet is less than about 1050 calories per day for two weeks, less than about 1,350 calories per day for two subsequent weeks, and less than about 1,550 calories per day for the subsequent weeks thereafter.

8. The method of claim 6 wherein the reduced-calorie diet includes at least 55% carbohydrates, from about 15% go about 28% protein, and less than 30% fat.

9. The method of claim 6 wherein said reduced calorie diet provides nutritional amounts of essential vitamins, minerals, and amino acids without supplementation with a multiple vitamin tablet.

10. A method of body weight management for an individual comprising:
orally administering to the individual in at least three approximately equal doses about 30 minutes before each daily meal a total daily amount of about 1,958 mg Garcinia cambogia extract, about 133 mg Gymnema sylvestre extract, about 2.5 mg chromium picolinate, about 0.09 mg bis-glycinato oxo vanadium, about 589 mg L-carnitine fumarate, about 1,800 mg conjugated linoleic acid, about 330 mg of kola nut extract, about 204 mg dehydrated parsley, and about 60 mg lemon bioflavonoids; and simultaneously restricting the individual to a reduced-calorie diet having a caloric intake less than the caloric expenditure of the individual and wherein said reduced-calorie diet is less than about 1050 calories per day for two weeks, less than about 1,350 calories per day for two subsequent weeks, and less than about 1,550 calories per day for the subsequent weeks thereafter.

11. A weight management support pack for reducing and/or managing body weight comprising from about 1,175 to about 2,741 mg Garcinia cambogia extract, from about 80 to about 186 mg Gymnema sylvestre extract, from about 1.5 to about 3.5 mg chromium picolinate, from about 0.05 to about 0.13 mg bis-glycinato oxo vanadium, from about 353 to about 825 mg L-carnitine fumarate, from about 1,080 to about 2,520 mg conjugated linoleic acid, from about 198 to about 396 mg kola nut extract, from about 122 to about 285 mg dehydrated parsley, and from about 36 to about 84 mg lemon bioflavonoids.

12. The weight management support pack of claim 11 comprising from about 1,566 to about 2,350 mg Garcinia cambogia extract, from about 106 to about 160 mg Gymnema sylvestre extract, from about 2 to about 3 mg chromium picolinate, about 0.07 to about 0.11 mg vanadium compound, from about 471 to about 707 mg L-carnitine, and from about 1,440 to about 2,160 mg conjugated linoleic acid.

13. The weight management support pack of claim 11 comprising about 1,958 mg Garcinia cambogia extract, about 133 mg Gymnema sylvestre extract, about 2.5 mg chromium picolinate, about 0.09 mg vanadium compound, about 589 mg L-carnitine, and about 1,800 mg conjugated linoleic acid.

14. The weight management support pack of claim 11 wherein the vanadium compound is a water-soluble vanadium chelate with amino acid.

15. The weight management support pack of claim 11, comprising about 1,958 mg Garcinia cambogia extract, about 133 mg Gymnema sylvestre extract, about 2.5 mg chromium picolinate, about 0.09 mg bis-glycinato oxo vanadium, about 589 mg L-carnitine fumarate, about 1,800 mg conjugated linoleic acid, about 330 mg of kola nut extract, about 204 mg dehydrated parsley, and about 60 mg lemon bioflavonoids.

16. The weight management support pack of claim 11 comprising three separate dietary supplements wherein a first dietary supplement is comprised of about 306 mg of the Garcinia cambogia extract, about 44 mg of the mg Gymnema sylvestre extract, about 0.84 mg of mg chromium picolinate, and about 0.03 mg bis-glycinato oxo vanadium, a second dietary supplement is comprised of about 347 mg of the Garcinia cambogia extract and about 197 mg of L-Carnitine Fumarate, and a third dietary supplement is comprised of about 525 mg of Conjugated Linoleic Acid and wherein each of the first, second, and third dietary supplements are taken three times per day.

* * * * *